United States Patent [19]

Hetherington

[11] Patent Number: Plant 6,984

[45] Date of Patent: Aug. 15, 1989

[54] ORCHID YAMADARA MIDNIGHT MAGENTA 'FINE WINE' AM/AOS

[75] Inventor: Ernest Hetherington, Arcadia, Calif.

[73] Assignee: Stewart Orchids, Carpenteria, Calif.

[21] Appl. No.: 163,940

[22] Filed: Mar. 3, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Howard A. Kenyon

[57] ABSTRACT

A new and distinct variety of orchid. More particularly a quadrigeneric orchid hybrid known as Yamadara Midnight Magenta 'Fine Wine' hybrid which is outstanding and distinct from other orchids because of its superior flowers which combine rare coloring, outstanding shape, number of flowers on the stem and excellent plant vigor. The coloring is rich dark burgundy wine throughout all parts of the flower. The new cultivar is also distinctive from its sibling population and similar hybrids by its outstanding plant vigor and reliability of bloom. Its flowers are of exceptional substance with thick and more resiliant petals than related siblings of the grex. They are perfectly placed on the stem; the stem is superior to its relatives in strength; the flowers have a longer bloom life and are produced more abundantly than orchids of the nearest similar breeding.

1 Drawing Sheet

DISCOVERY OF THE NEW VARIETY

The orchid of this application was discovered by the undersigned discoverer in March of 1979 as an outstanding member of a large sibling population of the hybrid Yamadara Midnight Magenta, hereinafter abbreviated as Yam. Midnight Magenta. All were cultivated and blooming at the Stewart Orchid Nursery in San Gabriel, Calif. The crossing of Yam. Midnight Magenta was by Dr. Harold Edelbrock of La Canada, Calif. The seedling was discovered as a first bloom plant in the nursery of Stewart Orchids by the applicant. The Yam. Midnight Magenta was a result of crossing Blc. Cinnamon Peak×Encyclia gracile and is a quadrigeneric hybrid. The grex was registered with The Royal Horticulture Society's orchid registration committee in London, England in 1972.

The plant of the new cultivar was immediately recognized as superior in its flowers to all members of that population of the hybrid grex, Yam. Midnight Magenta. After the new variety had been observed, its other features of super growth and structure were noted. The cultivar name 'Fine Wine' was added to the grex name of this cultivar by the applicant, to identify the new variety of this application.

After the 'Fine Wine' cultivar was discovered and named in 1979, the original plant was placed in the laboratories of Stewart Orchids. During the following years, a large number of plants have been asexually produced by the meristem tissue culture method. All propagations thus produced have reproduced true to the original plant in both plant and flower characteristics. A substantial cross section have been flowered; they are exactly the same as the mother clone. All plants of the new variety have continued to be readily distinguishable from both parents and from siblings of the Midnight Magenta grex population.

DESCRIPTION OF THE PHOTOGRAPH

The photograph is a close-up view of a spray of flowers typical of this new cultivar. The photograph especially shows the excellent placement of the flowers on the inflorescence as well as strength of stem to show how they are well carried.

DESCRIPTION OF THE PLANT

In some respects, the plant of the new variety 'Fine Wine' is typical of Cattleya and Laeliocattleya hybrids as far as growth habit is concerned. Its leaves are well-shaped, unifoliate and very coriaceous. The leaves at full growth are typically 30 to 35 centimeters. The plant obtains a height of 45 to 60 centimeters at maturity. However, the stems, flowers, leaves and other parts of the plant structure are heavier and thicker in appearance than other Midnight Magenta cultivars. The 'Fine Wine' cultivar exhibits greater strength and resilience than all other cultivars of Midnight Magenta. The rhizome is sturdy, branching off into several flowering leads. The growth habit is compact and naturally erect. The plant has a flower stem which bears the heavy textured flowers without support. The growths are of such substance, that the flowers are carried erectly and well spaced above the foliage and separate from other flowers on the plant at the same time. The plants are hardy in comparison with other similar lines of breeding because of the cold tolerant *Encyclia gracile* in the parentage. This is a very desirable characteristic of this cultivar. Yam. Midnight Magenta 'Fine Wine' plants, both in the original plant and in the tissue propagations have been virus and pathogen free during development. Representative samples are taken from the population to be virus tested. The plants have characteristics of a polyploid in that they have exceptional vigor for the grex and have strong uniform growth. There do not appear to be any characteristics of aneuploidy or aberrant growth habit. Characteristic of polyploidy also is the waving of the leaves.

DESCRIPTION OF THE FLOWERS

The outstanding merit and most distinguishing feature of the new variety is the richness of coloring of the flowers and their exceptional substance and long lasting qualities. The floral color and characteristic of this cultivar are described by reference to code numbers of The British Horticultural Colour Charts. Hereinafter referred to as B.H.C.C. numbers. The sepals and petals are of uniform color closest to pansy purple, page #177, color series 928, swatches 928-1 and 928. The color chart describes *Dipladenia atropurpurea* (outside of petals) as the nearest horticultural equivalent. The base of the dorsal sepal as it joins the column shades into uranium green, page #63, color series 63, swatch #63-3. Nearest horticultural equivalent Antirrhinum asarina. The lip is in nice balance with the flower. The basal and side lobes of the lip are folded out to open the lip. The lip color is closest to ruby red, horticultural color chart page 171, swatch series 87, swatch #827-1 to 827. No horticultural equivalents are given in the chart. The column of the flower is suffused Rhodamine pink, page #138, swatch series #527, swatch #527-1. Over this it is lightly stripping and spotted running the length of the sides in Indian Lake, page #170, swatch series #826, swatch #826-1 and 2. The nearest horticultural equivalent Nicotiana hybrid Sanderde. Of special note is the white pollen sac on the tip of the column which is small but clearly seen. Horticultural color chart color not shown. On close inspection, but covered by the labellum, the petals and two ventral sepals shade lightly and almost imperceptibly to the same color as the base of the dorsal sepal which is uranium green, page 63, color series 63, swatch 63-3.

The texture of both the sepals and petals is sparkling clear and of rich intense coloration. The flowers hold their color exceptionally well from opening to end of flower life. The flowers last for from two to five weeks. There are no cultivars of the grex Midnight Magenta which resemble the coloring or quality of the cultivar Fine Wine.

I claim:

1. A new and distinct variety of hybrid orchid substantially as described and illustrated herein and distinguised from its parents and siblings of the grex, Midnight Magenta and other orchids by its combination of rich flower coloring, superior flower substance, strength of stem structure, vigor of plant and reliable blooming.

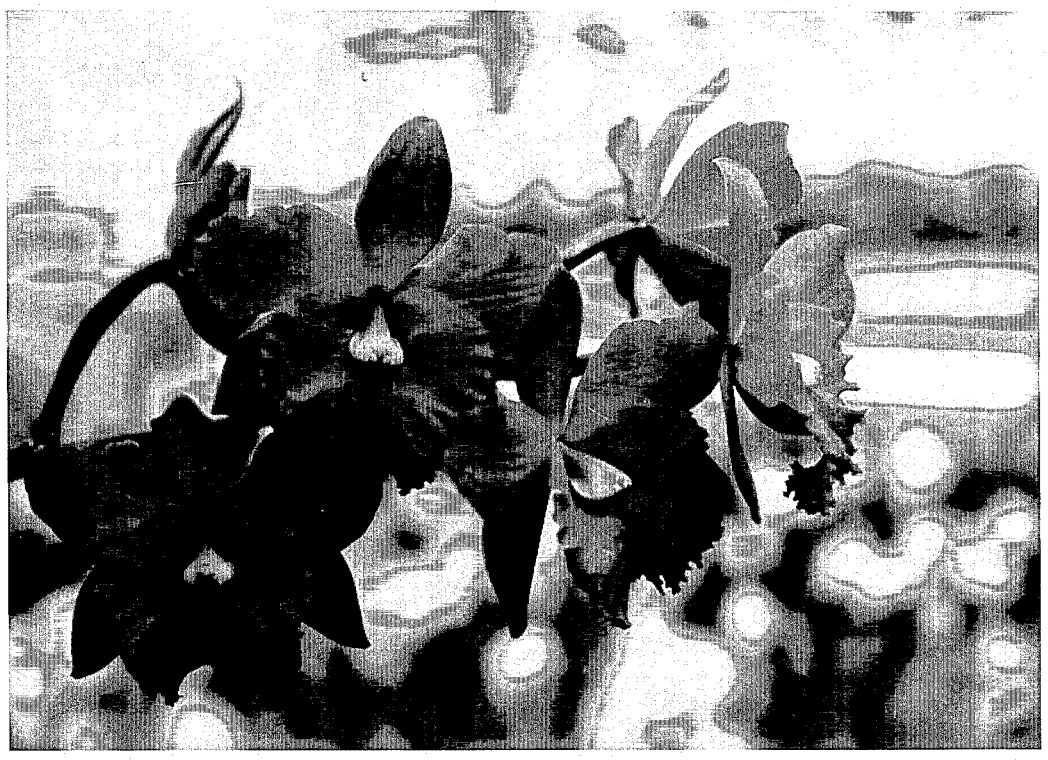

* * * * *